(12) United States Patent
Kumada et al.

(10) Patent No.: US 12,103,948 B2
(45) Date of Patent: Oct. 1, 2024

(54) SEPARATING AGENT

(71) Applicants: NATIONAL UNIVERSITY CORPORATION KYOTO INSTITUTE OF TECHNOLOGY, Kyoto (JP); DAICEL CORPORATION, Osaka (JP)

(72) Inventors: Yoichi Kumada, Kyoto (JP); Hiromichi Okura, Tokyo (JP); Seiichi Uchimura, Tokyo (JP)

(73) Assignees: NATIONAL UNIVERSITY CORPORATION KYOTO INSTITUTE OF TECHNOLOGY, Kyoto (JP); DAICEL CORPORATION, Osaka (JP)

( * ) Notice: Subject to any disclaimer, the term of this patent is extended or adjusted under 35 U.S.C. 154(b) by 862 days.

(21) Appl. No.: 17/256,599

(22) PCT Filed: Jul. 1, 2019

(86) PCT No.: PCT/JP2019/026134
§ 371 (c)(1),
(2) Date: Dec. 28, 2020

(87) PCT Pub. No.: WO2020/004668
PCT Pub. Date: Jan. 2, 2020

(65) Prior Publication Data
US 2021/0269476 A1    Sep. 2, 2021

(30) Foreign Application Priority Data
Jun. 29, 2018   (JP) ................. 2018-123978

(51) Int. Cl.
C07K 1/22   (2006.01)

(52) U.S. Cl.
CPC ..................... C07K 1/22 (2013.01)

(58) Field of Classification Search
CPC ............ C07K 1/22; C07K 2317/622; C07K 2317/92; C07K 16/42; B01D 15/3804
See application file for complete search history.

(56) References Cited

U.S. PATENT DOCUMENTS

| | | | |
|---|---|---|---|
| 2010/0286373 A1 | 11/2010 | Majima et al. | |
| 2013/0274446 A1 | 10/2013 | Kumagai et al. | |
| 2014/0107315 A1 | 4/2014 | Yoshida et al. | |
| 2016/0168209 A1 | 6/2016 | Yoshida et al. | |
| 2018/0327803 A1 | 11/2018 | Kumada et al. | |

FOREIGN PATENT DOCUMENTS

| | | |
|---|---|---|
| EP | 1 992 692 A1 | 11/2008 |
| EP | 2 690 173 A1 | 1/2014 |
| JP | 2007-252368 A | 10/2007 |
| JP | 2017-70289 A | 4/2017 |
| WO | WO 2012/020622 A1 | 2/2012 |
| WO | WO 2014/046278 A1 | 3/2014 |
| WO | WO 2017/082213 A1 | 5/2017 |
| WO | WO 2017/082214 A1 | 5/2017 |

OTHER PUBLICATIONS

Translation of WO2017082214A1 to Kumada retrieved from Espacenet on Sep. 11, 2023 from (https://worldwide.espacenet.com/patent/search/family/058695334/publication/WO2017082214A1?q=WO%202017%2F082214) (Year: 2017).*
Ueda, A., Umetsu, M., Nakanishi, T., Hashikami, K., Nakazawa, H., Hattori, S., . . . & Kumagai, I. (2020). Chemically crosslinked bispecific antibodies for cancer therapy: Breaking from the structural restrictions of the genetic fusion approach. International journal of molecular sciences, 21(3), 711. (Year: 2020).*
"L-Arginine." American Chemical Society, accessed on Feb. 5, 2024 from: www.acs.org/molecule-of-the-week/archive/a/l-arginine.html. (Year: 2024).*
International Preliminary Report on Patentability and Written Opinion mailed Jan. 7, 2021, in PCT/JP2019/026134.
International Search Report issued Jul. 30, 2019, in PCT/JP2019/026134.
Extended European Search Report for European Application No. 19825188.6, dated Aug. 24, 2021.
Pingali et al., "Peptides as Affinity Surfaces for Protein Purification," Journal of Molecular Recognition, vol. 9, 1996, pp. 426-432, 7 pages total.

* cited by examiner

*Primary Examiner* — Louise W Humphrey
*Assistant Examiner* — Kimberly Breen
(74) *Attorney, Agent, or Firm* — Birch, Stewart, Kolasch & Birch, LLP

(57) ABSTRACT

Provided is a separating agent with an improved dynamic binding capacity (DBC) to a target substance. The separating agent includes a carrier and a protein, wherein the protein is a given protein, and a surface of the carrier and added lysine residues in the protein are bound by chemical bonds.

5 Claims, 5 Drawing Sheets
Specification includes a Sequence Listing.

| CLONE NO. | V_H | | | |
|---|---|---|---|---|
| | FR1 | CDR1 | FR2 | CDR2 |
| R3-26 | QEQLVESGGGLVKPGGTLTLTCTV | SGIDLSSYA | MSWVRQVPGKGLEWIGI | IGSGGGT |
| R3-75 | QSVKESGGRLVTPGTPLTLTCTV | SGIDLSSNA | MSWVRQAPGEGLEWIGT | ISTVGKT |
| R3-23 | QSVKESEGRLVTPGTPLTLTCTV | SGFSLSRYA | VSWVRQAPGKGLEWIGI | IGSGGST |
| R3-58 | QQQLMESGGRLVTPGGSLTLTCTV | SGIDLNSYA | MGWVRQAPGKGLEYIGI | IRNSGNT |
| R2-18 | QSLEESGGRLVTPGTPLTLTCTV | SGIDLSSNA | MTWVRQAPGEGLEWIGT | ISTGGST |
| R2-16 | QSVKESGGRLVTPGTPLTLTCTV | SGFSLSSYA | MGWVRQAPGKGLEYIGI | ISSSGST |
| R1-27 | QQQLMESGGGLVTPGTPLTLTCTV | SGIDLRRYA | MGWVRQAPGKGLQWIGI | IASGNTD |
| R3-8 | QSLEESGGRLVTPGTPLTLTCTV | SGIDLSSNA | MTWVRQAPGEGLEWIGT | ISTGGST |
| R1-7 | QSLEESGGRLVTPGTPLTLTCTV | SGIDLRRYA | MGWVRQAPGKGLQWIGI | IASGNTD |

Fig. 2-1-1

| CLONE NO. | V_H | | | |
|---|---|---|---|---|
| | FR3 | CDR3 | FR4 | SEQ ID No. |
| R3-26 | AYANWAKGRFTISKTSSTTVDLKMTSLTTEDTATYFC | ATDYGIYGYAY GHLW | GPGTLVTVTS | 1 |
| R3-75 | YFASWAKGRFTISKT STTVDLRITSPTTEDTATYFC | ATRYDSYGYAYNYNWFGTLW | GPGTLVTVTS | 18 |
| R3-23 | SYATWARGRFTISKT STTVDLKITSPTTEDTVTYFC | GSYYDSHGYAY VSLW | GPGTLVTVTS | 19 |
| R3-58 | YYASWAKGRFTISKTSSTTVDLKMTSLTTEDTATYFC | ARYSGDNGGALN LW | GPGTLVTVTS | 20 |
| R2-18 | YFASWAKGRFTISKT STTVDLKITSPTTEDTATYFC | ATRYDSYGYAYNYNWFGTLW | GPGTLVTVTS | 21 |
| R2-16 | YYASWAKGRFTISKT STTVDLKITSPTTEDTATYFC | ARYSGDNGGALN LW | GPGTLVTVTS | 22 |
| R1-27 | YASWAKGRFTISAT STTVDLKITSSTTEDTATYFC | ARYSGDNGGTLN LW | GPGTLAIVTT | 23 |
| R3-8 | YFASWAKGRFTISKT STTVDLKITSPTTEDTATYFC | ATRYDSYGYAYNYNWFGTLW | GPGTLVTVTS | 24 |
| R1-7 | YASWAKGRFTISAT STTVDLKITSPTTEDTATYFC | ARYSGDNGGTLN LW | GPGTLVTVTS | 25 |

Fig. 2-1-2

| CLONE NO. | V_L ||||
|---|---|---|---|---|
| | FR1 | CDR1 | FR2 | CDR2 |
| R3-26 | ELVMTQTASPVSAAVGGTVTIKCQAS | QSISTA | LAWYQQRPGQPPKLLIY | DAS |
| R3-75 | ELDLTQTPPSVSGAVGGTVTIKCQAS | ENINSE | LAWYQQKPGQRPKLLIY | DAS |
| R3-23 | ELVLTQTPSPVSGAVGGTVTINCQAS | QSISTA | LAWYQQKPGQPPKLLIY | SAS |
| R3-58 | ELVMTQTAASVSGPVGGTVTIKCQAS | EFIRNY | LAWYQQKPGQPPKLLIY | TTS |
| R2-18 | ELVMTQTAASVSEPVGGTVTIKCQAS | QNINNE | LAWYQQKPGQRPKLLIY | DAS |
| R2-16 | ELDLTQTAASVSEPVGGTVTISCQSS | QHIRSY | LAWYQQKPGQPPKLLIS | AAS |
| R1-27 | ELVMTQTAASVSEPVGGTVTIKCQAS | EHIRNY | LAWYQQKPGQPPKLLIY | TTS |
| R3-8 | ELVMTQTAASVSEPVGGTVTINCQAS | QSISDE | LAWYQQKPGQRPKLLIY | DAS |
| R1-7 | ELVMTQTAASVSEPVGGTVTIKCQAS | QSISSY | LAWYQQKPGQPPKLLIY | AAS |

Fig. 2-2-1

| CLONE NO. | $V_L$ | | | SEQ ID No. |
|---|---|---|---|---|
| | FR3 | CDR3 | FR4 | |
| R3-26 | TLASGVSSRFKGSGSGSGTEFTLTISDLECADAATYYC | QTYFGSDTDNA | FGEGTEVEITGS | 3 |
| R3-75 | KLASGVPSRFSGSGSGSGTEYLTISGMQCDDAATYYC | QSTYYDGNYVYA | FGGGTEVDVTRS | 26 |
| R3-23 | TLASGVSSRFKGSGSGSGTGFTLTISDLECADAATYYC | QSYYGSSSDNA | FGGGTEVVIKRS | 27 |
| R3-58 | NLASGVPSRFSGSGSGSGTEYLTISDLECADAATYYC | QNYYDISTYGNA | FGGGTEVVVIKGS | 28 |
| R2-18 | KLASGVPSRFSGSGSGSGTEFTLTISGMQCDDAATYYC | QSTYYDGNYVYA | FGGGTEVDVKGS | 29 |
| R2-16 | TLASGVSSRFKGSGSGSGTEFTLTISDLECADAATYYC | QRYYDIRNYGNG | FGGGTEVEITGS | 30 |
| R1-27 | NLASGVPSRFSGSGSGSGTEYLTISDLECADAATYYC | QNYYDISTYGNT | FGGGTEVDVKGS | 31 |
| R3-8 | DLASGVPSRFSGSGSGSGTEFTLTISGVQCDDAATYYC | QSAYYDGRYVYA | FGGGTEVEVTGS | 32 |
| R1-7 | NLASGVSSRFKGSGSGSGTEFTLTISDLECADAATYYC | QSYYSISSYGNT | FGGGTEVEITGS | 33 |

SEQUENCE LISTING

<160> NUMBER OF SEQ ID NOS: 33

<210> SEQ ID NO 1
<211> LENGTH: 119
<212> TYPE: PRT
<213> ORGANISM: Oryctolagus cuniculus

<400> SEQUENCE: 1

Gln Glu Gln Leu Val Glu Ser Gly Gly Gly Leu Val Lys Pro Gly Gly
1               5                   10                  15

```
Thr Leu Thr Leu Thr Cys Thr Val Ser Gly Ile Asp Leu Ser Ser Tyr
            20                  25                  30

Ala Met Ser Trp Val Arg Gln Val Pro Gly Lys Gly Leu Glu Trp Ile
        35                  40                  45

Gly Ile Ile Gly Ser Gly Gly Thr Ala Tyr Ala Asn Trp Ala Lys
 50                  55                  60

Gly Arg Phe Thr Ile Ser Lys Thr Ser Ser Thr Val Asp Leu Lys
 65                  70                  75                  80

Met Thr Ser Leu Thr Thr Glu Asp Thr Ala Thr Tyr Phe Cys Ala Thr
            85                  90                  95

Asp Tyr Gly Ile Tyr Gly Tyr Ala Tyr Gly His Leu Trp Gly Pro Gly
            100                 105                 110

Thr Leu Val Thr Val Thr Ser
        115

<210> SEQ ID NO 2
<211> LENGTH: 15
<212> TYPE: PRT
<213> ORGANISM: Artificial Sequence
<220> FEATURE:
<223> OTHER INFORMATION: spacer

<400> SEQUENCE: 2

Gly Gly Gly Gly Ser Gly Gly Gly Gly Ser Gly Gly Gly Gly Ser
1               5                   10                  15

<210> SEQ ID NO 3
<211> LENGTH: 111
<212> TYPE: PRT
<213> ORGANISM: Oryctolagus cuniculus

<400> SEQUENCE: 3

Glu Leu Val Met Thr Gln Thr Ala Ser Pro Val Ser Ala Ala Val Gly
1               5                   10                  15

Gly Thr Val Thr Ile Lys Cys Gln Ala Ser Gln Ser Ile Ser Thr Ala
            20                  25                  30

Leu Ala Trp Tyr Gln Gln Arg Pro Gly Gln Pro Pro Lys Leu Leu Ile
        35                  40                  45

Tyr Asp Ala Ser Thr Leu Ala Ser Gly Val Ser Ser Arg Phe Lys Gly
 50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Thr Tyr Phe Gly Ser Asp Thr
            85                  90                  95

Asp Asn Ala Phe Gly Glu Gly Thr Glu Val Glu Ile Thr Gly Ser
            100                 105                 110

<210> SEQ ID NO 4
<211> LENGTH: 5
<212> TYPE: PRT
<213> ORGANISM: Artificial Sequence
<220> FEATURE:
<223> OTHER INFORMATION: spacer

<400> SEQUENCE: 4

Ala Ala Ala Leu Glu
1               5

<210> SEQ ID NO 5
```

```
<211> LENGTH: 250
<212> TYPE: PRT
<213> ORGANISM: Artificial Sequence
<220> FEATURE:
<223> OTHER INFORMATION: reference

<400> SEQUENCE: 5

Gln Glu Gln Leu Val Glu Ser Gly Gly Gly Leu Val Lys Pro Gly Gly
1               5                   10                  15

Thr Leu Thr Leu Thr Cys Thr Val Ser Gly Ile Asp Leu Ser Ser Tyr
            20                  25                  30

Ala Met Ser Trp Val Arg Gln Val Pro Gly Lys Gly Leu Glu Trp Ile
        35                  40                  45

Gly Ile Ile Gly Ser Gly Gly Thr Ala Tyr Ala Asn Trp Ala Lys
    50                  55                  60

Gly Arg Phe Thr Ile Ser Lys Thr Ser Ser Thr Thr Val Asp Leu Lys
65                  70                  75                  80

Met Thr Ser Leu Thr Thr Glu Asp Thr Ala Thr Tyr Phe Cys Ala Thr
                85                  90                  95

Asp Tyr Gly Ile Tyr Gly Tyr Ala Tyr Gly His Leu Trp Gly Pro Gly
            100                 105                 110

Thr Leu Val Thr Val Thr Ser Gly Gly Gly Ser Gly Gly Gly
        115                 120                 125

Ser Gly Gly Gly Ser Glu Leu Val Met Thr Gln Thr Ala Ser Pro
    130                 135                 140

Val Ser Ala Ala Val Gly Gly Thr Val Thr Ile Lys Cys Gln Ala Ser
145                 150                 155                 160

Gln Ser Ile Ser Thr Ala Leu Ala Trp Tyr Gln Gln Arg Pro Gly Gln
                165                 170                 175

Pro Pro Lys Leu Leu Ile Tyr Asp Ala Ser Thr Leu Ala Ser Gly Val
            180                 185                 190

Ser Ser Arg Phe Lys Gly Ser Gly Ser Gly Thr Glu Phe Thr Leu Thr
        195                 200                 205

Ile Ser Asp Leu Glu Cys Ala Asp Ala Ala Thr Tyr Tyr Cys Gln Thr
    210                 215                 220

Tyr Phe Gly Ser Asp Thr Asp Asn Ala Phe Gly Gly Gly Thr Glu Val
225                 230                 235                 240

Glu Ile Thr Gly Ser Ala Ala Ala Leu Glu
                245                 250

<210> SEQ ID NO 6
<211> LENGTH: 256
<212> TYPE: PRT
<213> ORGANISM: Artificial Sequence
<220> FEATURE:
<223> OTHER INFORMATION: comparative

<400> SEQUENCE: 6

Gln Glu Gln Leu Val Glu Ser Gly Gly Gly Leu Val Thr Pro Gly Gly
1               5                   10                  15

Thr Leu Thr Leu Thr Cys Thr Val Ser Gly Ile Asp Leu Ser Ser Tyr
            20                  25                  30

Ala Met Ser Trp Val Arg Gln Val Pro Gly Glu Gly Leu Glu Trp Ile
        35                  40                  45

Gly Ile Ile Gly Ser Gly Gly Thr Ala Tyr Ala Asn Trp Ala Arg
    50                  55                  60

Gly Arg Phe Thr Ile Ser Arg Thr Ser Ser Thr Thr Val Asp Leu Arg
```

```
                65                  70                  75                  80
Met Thr Ser Leu Thr Thr Glu Asp Thr Ala Thr Tyr Phe Cys Ala Thr
                            85                  90                  95

Asp Tyr Gly Ile Tyr Gly Tyr Ala Tyr Gly His Leu Trp Gly Pro Gly
                100                 105                 110

Thr Leu Val Thr Val Thr Ser Gly Gly Gly Ser Gly Gly Gly Gly
                115                 120                 125

Ser Gly Gly Gly Ser Glu Leu Val Met Gln Thr Ala Ser Pro
            130                 135                 140

Val Ser Ala Ala Val Gly Gly Thr Val Thr Ile Asn Cys Gln Ala Ser
145                 150                 155                 160

Gln Ser Ile Ser Thr Ala Leu Ala Trp Tyr Gln Gln Arg Pro Gly Gln
                165                 170                 175

Pro Pro Arg Leu Leu Ile Tyr Asp Ala Ser Thr Leu Ala Ser Gly Val
                180                 185                 190

Ser Ser Arg Phe Ser Gly Ser Gly Ser Gly Thr Glu Phe Thr Leu Thr
                195                 200                 205

Ile Ser Asp Leu Glu Ser Ala Asp Ala Ala Thr Tyr Tyr Cys Gln Thr
            210                 215                 220

Tyr Phe Gly Ser Asp Thr Asp Asn Ala Phe Gly Glu Gly Thr Glu Val
225                 230                 235                 240

Glu Ile Thr Gly Ser Ala Ala Gly Gly Gly Ser Lys Ile Glu
                245                 250                 255

<210> SEQ ID NO 7
<211> LENGTH: 258
<212> TYPE: PRT
<213> ORGANISM: Artificial Sequence
<220> FEATURE:
<223> OTHER INFORMATION: example

<400> SEQUENCE: 7

Gln Glu Gln Leu Val Glu Ser Gly Gly Gly Leu Val Thr Pro Gly Gly
1               5                   10                  15

Thr Leu Thr Leu Thr Cys Thr Val Ser Gly Ile Asp Leu Ser Ser Tyr
                20                  25                  30

Ala Met Ser Trp Val Arg Gln Val Pro Gly Glu Gly Leu Glu Trp Ile
                35                  40                  45

Gly Ile Ile Gly Ser Gly Gly Gly Thr Ala Tyr Ala Asn Trp Ala Arg
            50                  55                  60

Gly Arg Phe Thr Ile Ser Arg Thr Ser Ser Thr Thr Val Asp Leu Arg
65                  70                  75                  80

Met Thr Ser Leu Thr Thr Glu Asp Thr Ala Thr Tyr Phe Cys Ala Thr
                85                  90                  95

Asp Tyr Gly Ile Tyr Gly Tyr Ala Tyr Gly His Leu Trp Gly Pro Gly
                100                 105                 110

Thr Leu Val Thr Val Thr Ser Gly Gly Gly Ser Gly Gly Gly Gly
                115                 120                 125

Ser Gly Gly Gly Gly Ser Glu Leu Val Met Gln Thr Ala Ser Pro
            130                 135                 140

Val Ser Ala Ala Val Gly Gly Thr Val Thr Ile Asn Cys Gln Ala Ser
145                 150                 155                 160

Gln Ser Ile Ser Thr Ala Leu Ala Trp Tyr Gln Gln Arg Pro Gly Gln
                165                 170                 175

Pro Pro Arg Leu Leu Ile Tyr Asp Ala Ser Thr Leu Ala Ser Gly Val
```

```
                180                 185                 190
Ser Ser Arg Phe Ser Gly Ser Gly Ser Gly Thr Glu Phe Thr Leu Thr
            195                 200                 205

Ile Ser Asp Leu Glu Ser Ala Asp Ala Ala Thr Tyr Tyr Cys Gln Thr
            210                 215                 220

Tyr Phe Gly Ser Asp Thr Asp Asn Ala Phe Gly Gly Gly Thr Glu Val
225                 230                 235                 240

Glu Ile Thr Gly Ser Ala Ala Ala Gly Gly Gly Ser Lys Lys Lys
                245                 250                 255

Ile Glu

<210> SEQ ID NO 8
<211> LENGTH: 260
<212> TYPE: PRT
<213> ORGANISM: Artificial Sequence
<220> FEATURE:
<223> OTHER INFORMATION: example

<400> SEQUENCE: 8

Gln Glu Gln Leu Val Glu Ser Gly Gly Gly Leu Val Thr Pro Gly Gly
1               5                   10                  15

Thr Leu Thr Leu Thr Cys Thr Val Ser Gly Ile Asp Leu Ser Ser Tyr
            20                  25                  30

Ala Met Ser Trp Val Arg Gln Val Pro Gly Glu Gly Leu Glu Trp Ile
        35                  40                  45

Gly Ile Ile Gly Ser Gly Gly Thr Ala Tyr Ala Asn Trp Ala Arg
    50                  55                  60

Gly Arg Phe Thr Ile Ser Arg Thr Ser Thr Thr Val Asp Leu Arg
65              70                  75                  80

Met Thr Ser Leu Thr Thr Glu Asp Thr Ala Thr Tyr Phe Cys Ala Thr
                85                  90                  95

Asp Tyr Gly Ile Tyr Gly Tyr Ala Tyr Gly His Leu Trp Gly Pro Gly
            100                 105                 110

Thr Leu Val Thr Val Thr Ser Gly Gly Gly Ser Gly Gly Gly Gly
        115                 120                 125

Ser Gly Gly Gly Gly Ser Glu Leu Val Met Thr Gln Thr Ala Ser Pro
    130                 135                 140

Val Ser Ala Ala Val Gly Gly Thr Val Thr Ile Asn Cys Gln Ala Ser
145                 150                 155                 160

Gln Ser Ile Ser Thr Ala Leu Ala Trp Tyr Gln Gln Arg Pro Gly Gln
            165                 170                 175

Pro Pro Arg Leu Leu Ile Tyr Asp Ala Ser Thr Leu Ala Ser Gly Val
        180                 185                 190

Ser Ser Arg Phe Ser Gly Ser Gly Ser Gly Thr Glu Phe Thr Leu Thr
    195                 200                 205

Ile Ser Asp Leu Glu Ser Ala Asp Ala Ala Thr Tyr Tyr Cys Gln Thr
            210                 215                 220

Tyr Phe Gly Ser Asp Thr Asp Asn Ala Phe Gly Gly Gly Thr Glu Val
225                 230                 235                 240

Glu Ile Thr Gly Ser Ala Ala Ala Gly Gly Gly Ser Lys Lys Lys
                245                 250                 255

Lys Lys Ile Glu
            260

<210> SEQ ID NO 9
```

<211> LENGTH: 750
<212> TYPE: DNA
<213> ORGANISM: Artificial Sequence
<220> FEATURE:
<223> OTHER INFORMATION: reference

<400> SEQUENCE: 9

```
caggagcagc tggtggagtc cggggaggc ctggtcaagc ctggaggaac cctgacactc      60
acctgcacag tctctggaat cgacctcagt agctatgcaa tgagctgggt ccgccaggtt    120
ccagggaagg ggctggaatg gatcggaatc attggtagtg gtggtggcac agcctacgcg    180
aactgggcga aaggccgatt caccatctcc aaaacctcgt cgaccacggt ggatctgaaa    240
atgaccagtc tgacaaccga ggacacggcc acctatttct gtgccaccga ttacggcatt    300
tatggttatg cttatggtca cttgtggggc caggcaccc tcgtcaccgt cactagtggt     360
ggaggcggtt caggcggagg tggctctggc ggtggcggat ccgagctcgt gatgacccag    420
actgcatccc ccgtgtctgc agctgtggga ggcacagtca ccatcaagtg ccaggccagt    480
cagagcatta gcactgcatt agcctggtat cagcagagac agggcagcc tcccaagctc     540
ctgatctacg atgcatccac tctggcatct ggggtctcat cgcggttcaa aggcagtgga    600
tctgggacag agttcactct caccatcagc gacctgagt gtgccgatgc tgccacttac     660
tactgtcaaa cctattttgg tagtgatact gataatgctt tcggcgaagg gaccgaggtg    720
gagatcacag gttcggcggc cgcactcgag                                     750
```

<210> SEQ ID NO 10
<211> LENGTH: 768
<212> TYPE: DNA
<213> ORGANISM: Artificial Sequence
<220> FEATURE:
<223> OTHER INFORMATION: comparative

<400> SEQUENCE: 10

```
caggagcagc tggtggagtc cggggaggc ctggtcactc ctggaggaac cctgacactc      60
acctgcacag tctctggaat cgacctcagt agctatgcaa tgagctgggt ccgccaggtt    120
ccaggggaag ggctggaatg gatcggaatc attggtagtg gtggtggcac agcctacgcg    180
aactgggcgc gtggccgatt caccatctcc cgtacctcgt cgaccacggt ggatctgcgt    240
atgaccagtc tgacaaccga ggacacggcc acctatttct gtgccaccga ttacggcatt    300
tatggttatg cttatggtca cttgtggggc caggcaccc tcgtcaccgt cactagtggt     360
ggaggcggtt caggcggagg tggctctggc ggtggcggat ccgagctcgt gatgacccag    420
actgcatccc ccgtgtctgc agctgtggga ggcacagtca ccatcaattg ccaggccagt    480
cagagcatta gcactgcatt agcctggtat cagcagagac agggcagcc tccccgtctc     540
ctgatctacg atgcatccac tctggcatct ggggtctcat cgcggttctc tggcagtgga    600
tctgggacag agttcactct caccatcagc gacctggaga gtgccgatgc tgccacttac    660
tactgtcaaa cctattttgg tagtgatact gataatgctt tcggcgaagg gaccgaggtg    720
gagatcacag gttcggcggc cgcaggtgga ggcggttcaa aaatcgag                 768
```

<210> SEQ ID NO 11
<211> LENGTH: 774
<212> TYPE: DNA
<213> ORGANISM: Artificial Sequence
<220> FEATURE:
<223> OTHER INFORMATION: example

<400> SEQUENCE: 11

```
caggagcagc tggtggagtc cggggggaggc ctggtcactc ctggaggaac cctgacactc    60
acctgcacag tctctggaat cgacctcagt agctatgcaa tgagctgggt ccgccaggtt    120
ccaggggaag gctggaatg gatcggaatc attggtagtg gtggtggcac agcctacgcg     180
aactgggcgc gtggccgatt caccatctcc cgtacctcgt cgaccacggt ggatctgcgt    240
atgaccagtc tgacaaccga ggacacggcc acctatttct gtgccaccga ttacggcatt    300
tatggttatg cttatggtca cttgtggggc ccaggcaccc tcgtcaccgt cactagtggt    360
ggaggcggtt caggcggagg tggctctggc ggtggcggat ccgagctcgt gatgacccag    420
actgcatccc ccgtgtctgc agctgtggga ggcacagtca ccatcaattg ccaggccagt    480
cagagcatta gcactgcatt agcctggtat cagcagagac agggcagcc tccccgtctc     540 ctgatctacg atgcatccac tctggcatct ggggtctcat cgcggttctc tggcagtgga    600
tctgggacag agttcactct caccatcagc gacctggaga gtgccgatgc tgccacttac    660
tactgtcaaa cctattttgg tagtgatact gataatgctt tcggcgaagg gaccgaggtg    720
gagatcacag gttcggcggc cgcaggtgga ggcggttcaa aaagaaaat cgag           774
```

<210> SEQ ID NO 12
<211> LENGTH: 780
<212> TYPE: DNA
<213> ORGANISM: Artificial Sequence
<220> FEATURE:
<223> OTHER INFORMATION: example

<400> SEQUENCE: 12

```
caggagcagc tggtggagtc cggggggaggc ctggtcactc ctggaggaac cctgacactc    60
acctgcacag tctctggaat cgacctcagt agctatgcaa tgagctgggt ccgccaggtt    120
ccaggggaag gctggaatg gatcggaatc attggtagtg gtggtggcac agcctacgcg     180
aactgggcgc gtggccgatt caccatctcc cgtacctcgt cgaccacggt ggatctgcgt    240
atgaccagtc tgacaaccga ggacacggcc acctatttct gtgccaccga ttacggcatt    300
tatggttatg cttatggtca cttgtggggc ccaggcaccc tcgtcaccgt cactagtggt    360
ggaggcggtt caggcggagg tggctctggc ggtggcggat ccgagctcgt gatgacccag    420
actgcatccc ccgtgtctgc agctgtggga ggcacagtca ccatcaattg ccaggccagt    480
cagagcatta gcactgcatt agcctggtat cagcagagac agggcagcc tccccgtctc     540 ctgatctacg atgcatccac tctggcatct ggggtctcat cgcggttctc tggcagtgga    600
tctgggacag agttcactct caccatcagc gacctggaga gtgccgatgc tgccacttac    660
tactgtcaaa cctattttgg tagtgatact gataatgctt tcggcgaagg gaccgaggtg    720
gagatcacag gttcggcggc cgcaggtgga ggcggttcaa agaagaaaaa gaaaatcgag    780
```

<210> SEQ ID NO 13
<211> LENGTH: 8
<212> TYPE: PRT
<213> ORGANISM: Artificial Sequence
<220> FEATURE:
<223> OTHER INFORMATION: spacer

<400> SEQUENCE: 13

Ala Ala Ala Gly Gly Gly Gly Ser
1               5

<210> SEQ ID NO 14
<211> LENGTH: 11

```
<212> TYPE: PRT
<213> ORGANISM: Artificial Sequence
<220> FEATURE:
<223> OTHER INFORMATION: spacer

<400> SEQUENCE: 14

Ala Ala Ala Gly Gly Gly Gly Ser Lys Ile Glu
1               5                   10

<210> SEQ ID NO 15
<211> LENGTH: 13
<212> TYPE: PRT
<213> ORGANISM: Artificial Sequence
<220> FEATURE:
<223> OTHER INFORMATION: spacer

<400> SEQUENCE: 15

Ala Ala Ala Gly Gly Gly Gly Ser Lys Lys Lys Ile Glu
1               5                   10

<210> SEQ ID NO 16
<211> LENGTH: 15
<212> TYPE: PRT
<213> ORGANISM: Artificial Sequence
<220> FEATURE:
<223> OTHER INFORMATION: spacer

<400> SEQUENCE: 16

Ala Ala Ala Gly Gly Gly Gly Ser Lys Lys Lys Lys Lys Ile Glu
1               5                   10                  15

<210> SEQ ID NO 17
<211> LENGTH: 20
<212> TYPE: PRT
<213> ORGANISM: Artificial Sequence
<220> FEATURE:
<223> OTHER INFORMATION: spacer

<400> SEQUENCE: 17

Gly Gly Gly Gly Ser Gly Gly Gly Ser Gly Gly Gly Ser Gly
1               5                   10                  15

Gly Gly Gly Ser
            20

<210> SEQ ID NO 18
<211> LENGTH: 121
<212> TYPE: PRT
<213> ORGANISM: Oryctolagus cuniculus

<400> SEQUENCE: 18

Gln Ser Val Lys Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Ser Trp Val Arg Gln Ala Pro Gly Glu Gly Leu Glu Trp Ile Gly
        35                  40                  45

Thr Ile Ser Thr Val Gly Lys Thr Tyr Phe Ala Ser Trp Ala Lys Gly
    50                  55                  60

Arg Phe Thr Ile Ser Lys Thr Ser Thr Thr Val Asp Leu Arg Ile Thr
65                  70                  75                  80

Ser Pro Thr Thr Glu Asp Thr Ala Thr Tyr Phe Cys Ala Thr Arg Tyr
                85                  90                  95

Asp Ser Tyr Gly Tyr Ala Tyr Asn Tyr Trp Phe Gly Thr Leu Trp Gly
```

```
                100               105               110
Pro Gly Thr Leu Val Thr Val Thr Ser
        115               120

<210> SEQ ID NO 19
<211> LENGTH: 117
<212> TYPE: PRT
<213> ORGANISM: Oryctolagus cuniculus

<400> SEQUENCE: 19

Gln Ser Val Lys Glu Ser Glu Gly Arg Leu Val Thr Pro Gly Thr Pro
1               5                   10                  15

Leu Thr Leu Thr Cys Thr Val Ser Gly Phe Ser Leu Ser Arg Tyr Ala
            20                  25                  30

Val Ser Trp Val Arg Gln Ala Pro Gly Lys Gly Leu Glu Trp Ile Gly
        35                  40                  45

Ile Ile Gly Ser Gly Gly Ser Thr Ser Tyr Ala Thr Trp Ala Arg Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Val Thr Tyr Phe Cys Gly Ser Tyr Tyr
                85                  90                  95

Asp Ser His Gly Tyr Ala Tyr Val Ser Leu Trp Gly Pro Gly Thr Leu
                100                 105                 110

Val Thr Val Thr Ser
        115

<210> SEQ ID NO 20
<211> LENGTH: 118
<212> TYPE: PRT
<213> ORGANISM: Oryctolagus cuniculus

<400> SEQUENCE: 20

Gln Gln Gln Leu Met Glu Ser Gly Gly Arg Leu Val Thr Pro Gly Gly
1               5                   10                  15

Ser Leu Thr Leu Thr Cys Thr Val Ser Gly Ile Asp Leu Asn Ser Tyr
            20                  25                  30

Ala Met Gly Trp Val Arg Gln Ala Pro Gly Lys Gly Leu Glu Tyr Ile
        35                  40                  45

Gly Ile Ile Arg Asn Ser Gly Asn Thr Tyr Tyr Ala Ser Trp Ala Lys
    50                  55                  60

Gly Arg Phe Thr Ile Ser Lys Thr Ser Ser Thr Thr Val Asp Leu Lys
65                  70                  75                  80

Met Thr Ser Leu Thr Thr Glu Asp Thr Ala Thr Tyr Phe Cys Ala Arg
                85                  90                  95

Tyr Ser Gly Asp Asn Gly Gly Ala Leu Asn Leu Trp Gly Pro Gly Thr
                100                 105                 110

Leu Val Thr Val Thr Ser
        115

<210> SEQ ID NO 21
<211> LENGTH: 121
<212> TYPE: PRT
<213> ORGANISM: Oryctolagus cuniculus

<400> SEQUENCE: 21

Gln Ser Leu Glu Glu Ser Gly Gly Arg Leu Val Thr Pro Gly Thr Pro
1               5                   10                  15
```

Leu Thr Leu Thr Cys Thr Val Ser Gly Ile Asp Leu Ser Ser Asn Ala
            20                  25                  30

Met Thr Trp Val Arg Gln Ala Pro Gly Glu Gly Leu Glu Trp Ile Gly
        35                  40                  45

Thr Ile Ser Thr Gly Gly Ser Thr Tyr Phe Ala Ser Trp Ala Lys Gly
50                  55                  60

Arg Phe Thr Ile Ser Lys Thr Ser Thr Val Asp Leu Lys Ile Thr
65                  70                  75                  80

Ser Pro Thr Thr Glu Asp Thr Ala Thr Tyr Phe Cys Ala Thr Arg Tyr
                85                  90                  95

Asp Ser Tyr Gly Tyr Ala Tyr Asn Tyr Trp Phe Gly Thr Leu Trp Gly
            100                 105                 110

Pro Gly Thr Leu Val Thr Val Thr Ser
        115                 120

<210> SEQ ID NO 22
<211> LENGTH: 116
<212> TYPE: PRT
<213> ORGANISM: Oryctolagus cuniculus

<400> SEQUENCE: 22

Gln Ser Val Lys Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Gly Trp Val Arg Gln Ala Pro Gly Lys Gly Leu Glu Tyr Ile Gly
        35                  40                  45

Ile Ile Ser Ser Ser Gly Ser Thr Tyr Tyr Ala Ser Trp Ala Lys Gly
50                  55                  60

Arg Phe Thr Ile Ser Lys Thr Ser Thr Val Asp Leu Lys Ile Thr
65                  70                  75                  80

Ser Pro Thr Thr Glu Asp Thr Ala Thr Tyr Phe Cys Ala Arg Tyr Ser
                85                  90                  95

Gly Asp Asn Gly Gly Ala Leu Asn Leu Trp Gly Pro Gly Thr Leu Val
            100                 105                 110

Thr Val Thr Ser
        115

<210> SEQ ID NO 23
<211> LENGTH: 116
<212> TYPE: PRT
<213> ORGANISM: Oryctolagus cuniculus

<400> SEQUENCE: 23

Gln Gln Gln Leu Met Glu Ser Gly Gly Gly Leu Val Thr Pro Gly Thr
1               5                   10                  15

Pro Leu Thr Leu Thr Cys Thr Val Ser Gly Ile Asp Leu Arg Arg Tyr
            20                  25                  30

Ala Met Gly Trp Val Arg Gln Ala Pro Gly Lys Gly Leu Gln Trp Ile
        35                  40                  45

Gly Ile Ile Ala Ser Gly Asn Thr Asp Tyr Ala Ser Trp Ala Lys Gly
50                  55                  60

Arg Phe Thr Ile Ser Ala Thr Ser Thr Val Asp Leu Lys Ile Thr
65                  70                  75                  80

Ser Ser Thr Thr Glu Asp Thr Ala Thr Tyr Phe Cys Ala Arg Tyr Ser
                85                  90                  95

```
Gly Asp Asn Gly Gly Thr Leu Asn Leu Trp Gly Pro Gly Thr Leu Ala
                100                 105                 110

Thr Val Thr Thr
        115

<210> SEQ ID NO 24
<211> LENGTH: 121
<212> TYPE: PRT
<213> ORGANISM: Oryctolagus cuniculus

<400> SEQUENCE: 24

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Thr Trp Val Arg Gln Ala Pro Gly Glu Gly Leu Glu Trp Ile Gly
        35                  40                  45

Thr Ile Ser Thr Gly Gly Ser Thr Tyr Phe Ala Ser Trp Ala Lys Gly
    50                  55                  60

Arg Phe Thr Ile Ser Lys Thr Ser Thr Val Asp Leu Lys Ile Thr
65                  70                  75                  80

Ser Pro Thr Thr Glu Asp Thr Ala Thr Tyr Phe Cys Ala Thr Arg Tyr
                85                  90                  95

Asp Ser Tyr Gly Tyr Ala Tyr Asn Tyr Trp Phe Gly Thr Leu Trp Gly
                100                 105                 110

Pro Gly Thr Leu Val Thr Val Thr Ser
        115                 120

<210> SEQ ID NO 25
<211> LENGTH: 115
<212> TYPE: PRT
<213> ORGANISM: Oryctolagus cuniculus

<400> SEQUENCE: 25

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Arg Arg Tyr Ala
            20                  25                  30

Met Gly Trp Val Arg Gln Ala Pro Gly Lys Gly Leu Gln Trp Ile Gly
        35                  40                  45

Ile Ile Ala Ser Gly Asn Thr Asp Tyr Ala Ser Trp Ala Lys Gly Arg
    50                  55                  60

Phe Thr Ile Ser Ala Thr Ser Thr Thr Val Asp Leu Lys Ile Thr Ser
65                  70                  75                  80

Pro Thr Thr Glu Asp Thr Ala Thr Tyr Phe Cys Ala Arg Tyr Ser Gly
                85                  90                  95

Asp Asn Gly Gly Thr Leu Asn Leu Trp Gly Pro Gly Thr Leu Val Thr
                100                 105                 110

Val Thr Ser
    115

<210> SEQ ID NO 26
<211> LENGTH: 112
<212> TYPE: PRT
<213> ORGANISM: Oryctolagus cuniculus

<400> SEQUENCE: 26
```

```
Glu Leu Asp Leu Thr Gln Thr Pro Pro Ser Val Ser Gly Ala Val Gly
1               5                   10                  15

Gly Thr Val Thr Ile Lys Cys Gln Ala Ser Glu Asn Ile Asn Ser Glu
            20                  25                  30

Leu Ala Trp Tyr Gln Gln Lys Pro Gly Gln Arg Pro Lys Leu Leu Ile
        35                  40                  45

Tyr Asp Ala Ser Lys Leu Ala Ser Gly Val Pro Ser Arg Phe Ser Gly
    50                  55                  60

Ser Gly Ser Gly Thr Glu Tyr Thr Leu Thr Ile Ser Gly Met Gln Cys
65                  70                  75                  80

Asp Asp Ala Ala Thr Tyr Tyr Cys Gln Ser Thr Tyr Tyr Asp Gly Asn
                85                  90                  95

Tyr Val Tyr Ala Phe Gly Gly Gly Thr Glu Val Asp Val Thr Arg Ser
            100                 105                 110
```

<210> SEQ ID NO 27
<211> LENGTH: 111
<212> TYPE: PRT
<213> ORGANISM: Oryctolagus cuniculus

<400> SEQUENCE: 27

```
Glu Leu Val Leu Thr Gln Thr Pro Ser Pro Val Ser Gly Ala Val Gly
1               5                   10                  15

Gly Thr Val Thr Ile Asn Cys Gln Ala Ser Gln Ser Ile Ser Thr Ala
            20                  25                  30

Leu Ala Trp Tyr Gln Gln Lys Pro Gly Gln Pro Pro Lys Leu Leu Ile
        35                  40                  45

Tyr Ser Ala Ser Thr Leu Ala Ser Gly Val Ser Ser Arg Phe Lys Gly
    50                  55                  60

Ser Gly Ser Gly Thr Gly Phe Thr Leu Thr Ile Ser Asp Leu Glu Cys
65                  70                  75                  80

Ala Asp Ala Ala Thr Tyr Tyr Cys Phe Gly Gly Thr Glu Val Val
                85                  90                  95

Ile Lys Arg Ser Gln Ser Tyr Tyr Gly Ser Ser Ser Asp Asn Ala
            100                 105                 110
```

<210> SEQ ID NO 28
<211> LENGTH: 113
<212> TYPE: PRT
<213> ORGANISM: Oryctolagus cuniculus

<400> SEQUENCE: 28

```
Glu Leu Val Met Thr Gln Thr Ala Ala Ser Val Ser Gly Pro Val Gly
1               5                   10                  15

Gly Thr Val Thr Ile Lys Cys Gln Ala Ser Glu Phe Ile Arg Asn Tyr
            20                  25                  30

Leu Ala Trp Tyr Gln Gln Lys Pro Gly Gln Pro Pro Lys Leu Leu Ile
        35                  40                  45

Tyr Thr Thr Ser Asn Leu Ala Ser Gly Val Pro Ser Arg Phe Ser Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Asn Tyr Tyr Asp Ile Ser Thr
                85                  90                  95

Tyr Gly Asn Ala Phe Gly Gly Thr Glu Val Val Val Ile Lys Gly
            100                 105                 110
```

Ser

<210> SEQ ID NO 29
<211> LENGTH: 112
<212> TYPE: PRT
<213> ORGANISM: Oryctolagus cuniculus

<400> SEQUENCE: 29

Glu Leu Val Met Thr Gln Thr Ala Ala Ser Val Ser Glu Pro Val Gly
1               5                   10                  15

Gly Thr Val Thr Ile Lys Cys Gln Ala Ser Gln Asn Ile Asn Asn Glu
            20                  25                  30

Leu Ala Trp Tyr Gln Gln Lys Pro Gly Gln Arg Pro Lys Leu Leu Ile
        35                  40                  45

Tyr Asp Ala Ser Lys Leu Ala Ser Gly Val Pro Ser Arg Phe Ser Gly
    50                  55                  60

Ser Gly Ser Gly Thr Glu Phe Thr Leu Thr Ile Ser Gly Met Gln Cys
65                  70                  75                  80

Asp Asp Ala Ala Thr Tyr Tyr Cys Gln Ser Thr Tyr Tyr Asp Gly Asn
                85                  90                  95

Tyr Val Tyr Ala Phe Gly Gly Gly Thr Glu Val Asp Val Lys Gly Ser
            100                 105                 110

<210> SEQ ID NO 30
<211> LENGTH: 112
<212> TYPE: PRT
<213> ORGANISM: Oryctolagus cuniculus

<400> SEQUENCE: 30

Glu Leu Asp Leu Thr Gln Thr Ala Ala Ser Val Ser Glu Pro Val Gly
1               5                   10                  15

Gly Thr Val Thr Ile Ser Cys Gln Ser Ser Gln His Ile Arg Ser Tyr
            20                  25                  30

Leu Ala Trp Tyr Gln Gln Lys Pro Gly Gln Pro Pro Lys Leu Leu Ile
        35                  40                  45

Ser Ala Ala Ser Thr Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Arg Tyr Tyr Asp Ile Arg Asn
                85                  90                  95

Tyr Gly Asn Gly Phe Gly Gly Gly Thr Glu Val Glu Ile Thr Gly Ser
            100                 105                 110

<210> SEQ ID NO 31
<211> LENGTH: 112
<212> TYPE: PRT
<213> ORGANISM: Oryctolagus cuniculus

<400> SEQUENCE: 31

Glu Leu Val Met Thr Gln Thr Ala Ala Ser Val Ser Glu Pro Val Gly
1               5                   10                  15

Gly Thr Val Thr Ile Lys Cys Gln Ala Ser Glu His Ile Arg Asn Tyr
            20                  25                  30

Leu Ala Trp Tyr Gln Gln Lys Pro Gly Gln Pro Pro Lys Leu Leu Ile
        35                  40                  45

Tyr Thr Thr Ser Asn Leu Ala Ser Gly Val Pro Ser Arg Phe Ser Gly
    50                  55                  60

```
Ser Gly Ser Gly Thr Glu Tyr Thr Leu Thr Ile Ser Asp Leu Glu Cys
 65                  70                  75                  80

Ala Asp Ala Ala Thr Tyr Tyr Cys Gln Asn Tyr Tyr Asp Ile Ser Thr
                 85                  90                  95

Tyr Gly Asn Thr Phe Gly Gly Gly Thr Glu Val Asp Val Lys Gly Ser
            100                 105                 110

<210> SEQ ID NO 32
<211> LENGTH: 112
<212> TYPE: PRT
<213> ORGANISM: Oryctolagus cuniculus

<400> SEQUENCE: 32

Glu Leu Val Met Thr Gln Thr Ala Ala Ser Val Ser Glu Pro Val Gly
 1               5                  10                  15

Gly Thr Val Thr Ile Asn Cys Gln Ala Ser Gln Ser Ile Ser Asp Glu
                 20                  25                  30

Leu Ala Trp Tyr Gln Gln Lys Pro Gly Gln Arg Pro Lys Leu Leu Ile
             35                  40                  45

Tyr Asp Ala Ser Asp Leu Ala Ser Gly Val Pro Ser Arg Phe Ser Gly
         50                  55                  60

Ser Gly Ser Gly Thr Glu Phe Thr Leu Thr Ile Ser Gly Val Gln Cys
 65                  70                  75                  80

Asp Asp Ala Ala Thr Tyr Tyr Cys Gln Ser Ala Tyr Tyr Asp Gly Arg
                 85                  90                  95

Tyr Val Tyr Ala Phe Gly Gly Gly Thr Glu Val Glu Val Thr Gly Ser
            100                 105                 110

<210> SEQ ID NO 33
<211> LENGTH: 112
<212> TYPE: PRT
<213> ORGANISM: Oryctolagus cuniculus

<400> SEQUENCE: 33

Glu Leu Val Met Thr Gln Thr Ala Ala Ser Val Ser Glu Pro Val Gly
 1               5                  10                  15

Gly Thr Val Thr Ile Lys Cys Gln Ala Ser Gln Ser Ile Ser Ser Tyr
                 20                  25                  30

Leu Ala Trp Tyr Gln Gln Lys Pro Gly Gln Pro Pro Lys Leu Leu Ile
             35                  40                  45

Tyr Ala Ala Ser Asn Leu Ala Ser Gly Val Ser Ser Arg Phe Lys Gly
         50                  55                  60

Ser Gly Ser Gly Thr Glu Phe Thr Leu Thr Ile Ser Asp Leu Glu Cys
 65                  70                  75                  80

Ala Asp Ala Ala Thr Tyr Tyr Cys Gln Ser Tyr Tyr Ser Ile Ser Ser
                 85                  90                  95

Tyr Gly Asn Thr Phe Gly Gly Gly Thr Glu Val Glu Ile Thr Gly Ser
            100                 105                 110
```

SEPARATING AGENT

TECHNICAL FIELD

The present disclosure relates to a separating agent.

BACKGROUND ART

Various technological developments have been made to improve the performance of affinity chromatography columns so far. For example, substitution of all lysine residues present in protein A with other amino acid residues and addition of a lysine residue to a terminus allow the protein A to be immobilized on a carrier via the ε-amino group of the side chain thereof. A column thus produced has maximized binding capacity and binding efficiency to a target substance (Patent Document 1).

On the other hand, a method is known in which the variable region of an antibody is expressed as a single-chain antibody (scFv) on a phage surface by the phage display method, and a phage binding to a desired antigen is selected. The DNA sequence encoding the single-chain antibody binding to the antigen can be determined by analysis of the gene of the selected phage. In addition, use of the single-chain antibody binding to the antigen can produce a separating agent for the antigen. To produce a separating agent for an antigen using a single-chain antibody, the separating agent is typically produced by binding the single-chain antibody to a carrier of the separating agent (Patent Documents 2 and 3).

CITATION LIST

Patent Document

Patent Document 1: JP 2017-070289A
Patent Document 2: WO 2017/08221
Patent Document 3: WO 2017/082214

SUMMARY OF DISCLOSURE

Technical Problem

The present inventors have found that for binding a single-chain antibody to a surface of a carrier to produce a separating agent for separating a target substance from a mixed liquid of two or more water-soluble substances, binding the single-chain antibody via a lysine residue originally contained therein may reduce a dynamic binding capacity (DBC) of the separating agent to the target substance depending on the amino acid sequence contained in the single-chain antibody.

An object of the present disclosure is to provide a separating agent with an improved dynamic binding capacity (DBC) to a target substance.

Solution to Problem

The present inventors found that the above objects can be solved by employing the following constitutions (1) to (3) as the separating agent.

(1) Lysine residues originally contained in the single-chain antibody included in the separating agent are substituted with amino acid residues other than a lysine residue.

(2) An amino acid sequence containing three or more lysine residues is contained at the C-terminus of the protein included in the separating agent.

(3) A surface of the carrier and lysine residues in the amino acid sequence containing three or more lysine residues are bound by chemical bonds.

The above is specifically described as follows.

A separating agent including a carrier and a protein, wherein
the protein is a protein containing:
an amino acid sequence represented by SEQ ID NO: 1, an amino acid sequence represented by SEQ ID NO: 2, and an amino acid sequence represented by SEQ ID NO: 3 arranged sequentially from the N-terminus; or
an amino acid sequence represented by SEQ ID NO: 3, an amino acid sequence represented by SEQ ID NO: 17, and an amino acid sequence represented by SEQ ID NO: 1 arranged sequentially from the N-terminus; and
an amino acid sequence containing three or more lysine residues at the C-terminus;
all lysine residues contained in the amino acid sequence represented by SEQ ID NO: 1, the amino acid sequence represented by SEQ ID NO: 2, the amino acid sequence represented by SEQ ID NO: 17, and the amino acid sequence represented by SEQ ID NO: 3 are substituted with amino acid residues other than a lysine residue; and
a surface of the carrier and lysine residues in the amino acid sequence containing three or more lysine residues are bound by chemical bonds.

In addition, another aspect of the present disclosure is a method for separating a water-soluble substance with the protein bound from a mixed liquid of two or more water-soluble substances using the separating agent described above.

Furthermore, another aspect of the present disclosure is a protein containing:
an amino acid sequence represented by SEQ ID NO: 1, an amino acid sequence represented by SEQ ID NO: 2, and an amino acid sequence represented by SEQ ID NO: 3 arranged sequentially from the N-terminus; or
an amino acid sequence represented by SEQ ID NO: 3, an amino acid sequence represented by SEQ ID NO: 17, and an amino acid sequence represented by SEQ ID NO: 1 arranged sequentially from the N-terminus; and
an amino acid sequence containing three or more lysine residues at the C-terminus;
wherein all lysine residues contained in the amino acid sequence represented by SEQ ID NO: 1, the amino acid sequence represented by SEQ ID NO: 2, the amino acid sequence represented by SEQ ID NO: 17, and the amino acid sequence represented by SEQ ID NO: 3 are substituted with amino acid residues other than a lysine residue.

Advantageous Effects of Disclosure

The present disclosure can provide a separating agent with an improved dynamic binding capacity (DBC) to a target substance. In addition, the present disclosure can provide a method for separating a target substance from a mixed liquid of two or more water-soluble substances using the separating agent.

BRIEF DESCRIPTION OF DRAWINGS

- FIG. 2-1-1 is a diagram showing an amino acid sequence represented by SEQ ID NO: 1 and amino acid sequences substantially identical to the amino acid sequence represented by SEQ ID NO: 1 according to an embodiment of the present disclosure.

FIG. 2-1-2 is a diagram showing an amino acid sequence represented by SEQ ID NO: 1 and amino acid sequences substantially identical to the amino acid sequence represented by SEQ ID NO: 1 according to an embodiment of the present disclosure.

FIG. 2-2-1 is a diagram showing an amino acid sequence represented by SEQ ID NO: 3 and amino acid sequences substantially identical to the amino acid sequence represented by SEQ ID NO: 3 according to an embodiment of the present disclosure.

FIG. 2-2-2 is a diagram showing an amino acid sequence represented by SEQ ID NO: 3 and amino acid sequences substantially identical to the amino acid sequence represented by SEQ ID NO: 3 according to an embodiment of the present disclosure.

DESCRIPTION OF EMBODIMENTS

Figure 1:
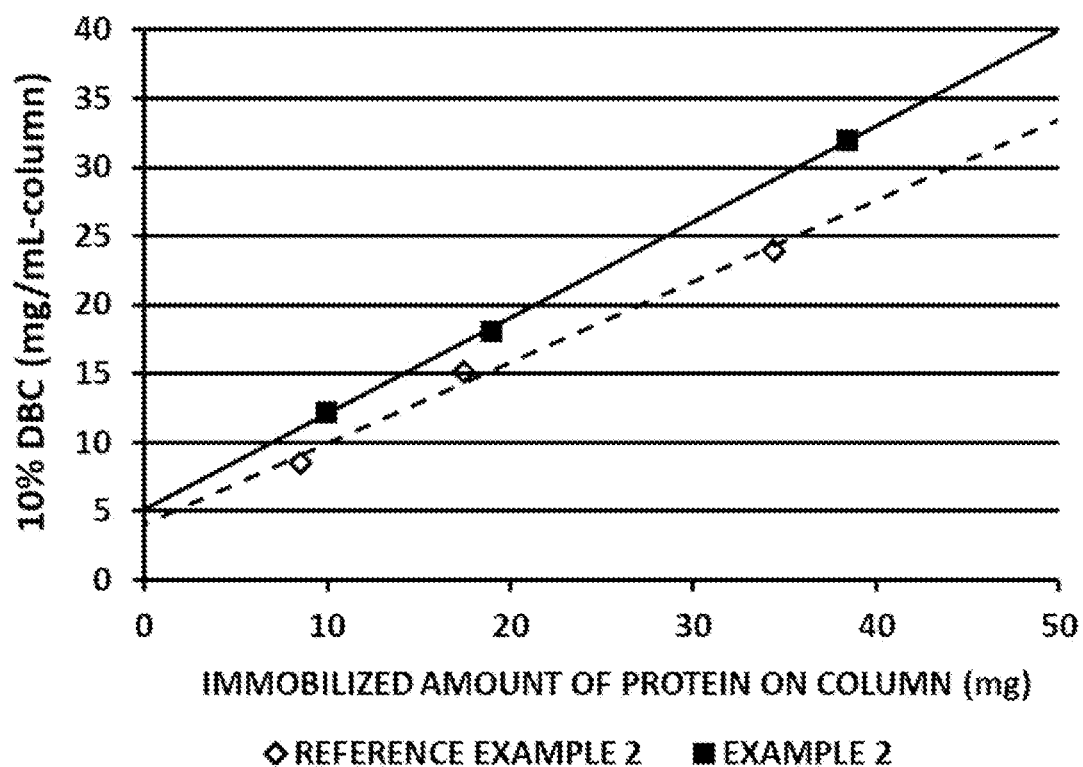
FIG. 1 is a graph showing the relationship between the amount of a protein immobilized on an affinity chromatog

The present disclosure includes an aspect related to a separating agent (a first aspect of the present disclosure) and an aspect related to a method for separating a water-soluble substance with the protein bound from a mixed liquid of two or more water-soluble substances using the separating agent (a second aspect of the present disclosure).

A single-chain antibody may be referred to in the art, for example, as a single-chain Fv (scFv) as one of low molecular weight antibodies. In addition, the single-chain antibodies described in the present specification also include a single-chain antibody derived from a rabbit, but this is merely an example where the single-chain antibody is derived from a rabbit, and the single-chain antibodies described in the present specification are not limited to a single-chain antibody derived from a rabbit.

1. First Aspect of Disclosure

A first aspect of the present disclosure is
a separating agent including a carrier and a protein, wherein
the protein is a protein containing:
an amino acid sequence represented by SEQ ID NO: 1, an amino acid sequence represented by SEQ ID NO: 2, and an amino acid sequence represented by SEQ ID NO: 3 arranged sequentially from the N-terminus; or
an amino acid sequence represented by SEQ ID NO: 3, an amino acid sequence represented by SEQ ID NO: 17, and an amino acid sequence represented by SEQ ID NO: 1 arranged sequentially from the N-terminus; and
an amino acid sequence containing three or more lysine residues at the C-terminus;
all lysine residues contained in the amino acid sequence represented by SEQ ID NO: 1, the amino acid sequence represented by SEQ ID NO: 2, the amino acid sequence represented by SEQ ID NO: 17, and the amino acid sequence represented by SEQ ID NO: 3 are substituted with amino acid residues other than a lysine residue; and
a surface of the carrier and lysine residues in the amino acid sequence containing three or more lysine residues are bound by chemical bonds.

[Carrier]

The carrier used in the first aspect of the present disclosure is preferably a water-insoluble carrier. Examples of the water-insoluble carrier include inorganic carriers, such as glass beads and silica gels; organic carriers composed of a synthetic polymer, such as a crosslinked polyvinyl alcohol, a crosslinked polyacrylate, a crosslinked polyacrylamide, or a crosslinked polystyrene, or a polysaccharide, such as a crystalline cellulose, a crosslinked cellulose, a crosslinked agarose, or a crosslinked dextran; and composite carriers obtained by combining these carriers, such as organic-organic or organic-inorganic composite carriers. Among these carriers, a hydrophilic carrier has relatively low non-specific adsorption and good selectivity for the protein used in the first aspect of the present disclosure and thus is preferred. The hydrophilic carrier as used herein refers to a carrier having a contact angle with water of 60 degrees or less as measured when a compound constituting the carrier is formed into a flat plate shape. Examples of such carriers include polysaccharides, such as cellulose, chitosan, and dextran; polyvinyl alcohol; a saponified product of an ethylene-vinyl acetate copolymer; polyacrylamide; polyacrylic acid; polymethacrylic acid; methyl polymethacrylate; polyacrylic acid-grafted polyethylene; polyacrylamide-grafted polyethylene; and glass.

Commercially available carriers can be exemplified by GCL2000 and GC700, which are porous cellulose gels; Sephacryl S-1000, obtained by covalently crosslinking allyl dextran and methylenebisacrylamide; Toyopearl, which is an acrylate-based carrier; Sepharose CL4B, which is an agarose-based crosslinked carrier; and Eupergit C250L, which is a polymethacrylamide activated with epoxy groups. In the first aspect of the present disclosure, however, the carrier is not limited to only these carriers or activated carriers. The carriers described above may be used alone, or any two or more may be mixed. In addition, in view of the intended use and method of the present separating agent, the water-insoluble carrier used in the first aspect of the present disclosure desirably has large surface area and thus preferably has many pores with suitable size, that is, the water-insoluble carrier is preferably porous.

The carrier can be in any form, such as beads, fibers, and membranes (including hollow fibers), and a carrier in any form can be selected. A carrier in the form of beads is particularly preferably used because of ease of preparing a carrier having a specific exclusion limit molecular weight. A carrier in the form of beads with an average particle size from 10 to 2500 μm is easy to use, and in particular, a carrier with an average particle size ranging from 25 μm to 800 μm is preferred because of ease of immobilization of the protein used in the first aspect of the present disclosure on the carrier surface via added lysine residues.

Furthermore, it is favorable that a functional group that can be used in a chemical bonding reaction with lysine residues in the amino acid sequences containing three or more lysine residues in the protein used in the first aspect of the present disclosure is present on the carrier surface. Representative examples of the functional group include a hydroxyl group, an amino group, an aldehyde group, a carboxyl group, a thiol group, a silanol group, an amide group, an epoxy group, a succinylimide group, an acid anhydride group, and an iodoacetyl group.

[Chemical Bond Between Added Lysine and Carrier Surface]

Examples of a method for chemically bonding the carrier surface and the protein used in the first aspect of the present disclosure via lysine residues in the amino acid sequence containing three or more lysine residues in the protein (an immobilization method) include a method of chemically bonding via ε-amino groups of the lysine residues, including, for example, a method of covalently bonding the protein to the carrier by a coupling method known in the art. Examples of the coupling method include methods commonly employed for immobilizing a protein or a peptide on a carrier. Examples include a method of reacting the carrier with cyanogen bromide, epichlorohydrin, diglycidyl ether, tosyl chloride, tresyl chloride, hydrazine, sodium periodate, or the like to activate the carrier (or introducing a reactive functional group to the carrier surface) and then performing a coupling reaction with the lysine residue; and a method of adding a condensation reagent, such as carbodiimide, or a reagent having a plurality of functional groups in a molecule, such as glutaraldehyde, into a system with the carrier and the lysine residue present, to condense or crosslink them. It is more preferred, however, to use a bonding method that allows the lysine residue not to be easily eliminated from the carrier during sterilization or use of the separating agent. In addition, a spacer molecule composed of a plurality of atoms may be introduced between the lysine residue and the carrier, or the lysine residue may be directly immobilized on the carrier.

Specific examples of chemically bonding the carrier surface and the protein used in the first aspect of the present disclosure via lysine residues in the amino acid sequence containing three or more lysine residues in the protein include an immobilization method using HiTrap NHS-activated HP Columns (GE Healthcare Inc.) as described in Examples.

[Protein]

The protein used in the first aspect of the present disclosure is a protein containing:
an amino acid sequence represented by SEQ ID NO: 1, an amino acid sequence represented by SEQ ID NO: 2, and an amino acid sequence represented by SEQ ID NO: 3 arranged sequentially from the N-terminus; or
an amino acid sequence represented by SEQ ID NO: 3, an amino acid sequence represented by SEQ ID NO: 17, and an amino acid sequence represented by SEQ ID NO: 1 arranged sequentially from the N-terminus; and
an amino acid sequence containing three or more lysine residues at the C-terminus;
wherein all lysine residues contained in the amino acid sequence represented by SEQ ID NO: 1, the amino acid sequence represented by SEQ ID NO: 2, the amino acid sequence represented by SEQ ID NO: 17, and the amino acid sequence represented by SEQ ID NO: 3 are substituted with amino acid residues other than a lysine residue.

The amino acid sequence represented by SEQ ID NO: 1 is an amino acid sequence of a heavy chain (H chain) variable region ($V_H$ domain) in a single-chain antibody R3-26 described in Patent Documents 2 and 3.

The amino acid sequence represented by SEQ ID NO: 3 is an amino acid sequence of a light chain (L chain) variable region ($V_L$ domain) in the single-chain antibody R3-26 described in Patent Documents 2 and 3.

The amino acid sequence represented by SEQ ID NO: 2 and the amino acid sequence represented by SEQ ID NO: 17 are linker sequences linking the $V_H$ domain and the $V_L$ domain in the single-chain antibody R3-26 described in Patent Documents 2 and 3.

The protein used in the first aspect of the present disclosure is bound by chemical bonds on the surface of the carrier via lysine residues in the amino acid sequence containing three or more lysine residues. The amino acid sequence containing three or more lysine residues has preferably three or more amino acid residues, more preferably four or more amino acid residues, and even more preferably five or more amino acid residues. On the other hand, in terms of bonding the protein with another linker amino acid sequence or another protein, the amino acid sequence containing three or more lysine residues has preferably 1000 or less amino acid residues, more preferably 100 or less amino acid residues, and even more preferably 15 or less amino acid residues.

In addition, the amino acid sequence containing three or more lysine residues has preferably four or more lysine residues and more preferably five or more lysine residues, and the upper limit of the number of lysine residues is preferably 1000 or less, more preferably 100 or less, and even more preferably 10 or less lysine residues. Furthermore, when a plurality of lysine residues are added, the lysine residues need not be consecutive (adjacent), and as long as the effects of the present disclosure can be achieved, an amino acid residue other than a lysine residue may be contained between the lysine residues, but the lysine residues are preferably consecutive (adjacent).

The amino acid sequence containing three or more lysine residues is preferably an amino acid sequence in which AAAGGGGS (SEQ ID NO: 13) is present on the N-terminus side of consecutive three or more lysine residues, and IE is present on the C-terminus side of the consecutive three or more lysine residues.

Referring to Patent Documents 2 and 3, it can be understood that the single-chain antibody R3-26 recognizes and binds to a human serum-derived IgG polyclonal antibody. Furthermore, referring to Patent Documents 2 and 3, it can be understood that the single-chain antibody R3-26 recognizes and binds to one or more antibodies selected from the group consisting of a human serum-derived IgG1 polyclonal antibody, a human serum-derived IgG2 polyclonal antibody, a human serum-derived IgG3 polyclonal antibody, and a human serum-derived IgG4 polyclonal antibody, which are subtypes of a human serum-derived IgG polyclonal antibody. The single-chain antibody R3-26 is a single-chain antibody derived from a rabbit, but the animal from which the single-chain antibody is derived is not particularly limited. Examples of the animal from which the single-chain antibody is derived include a human, a rat, a mouse, a rabbit, a chicken, a goat, a sheep, a cow, a horse, a dog, a cat, and a monkey.

In the protein used in the first aspect of the present disclosure, all lysine residues contained in the amino acid sequence represented by SEQ ID NO: 1, the amino acid sequence represented by SEQ ID NO: 2, the amino acid sequence represented by SEQ ID NO: 17, and the amino acid sequence represented by SEQ ID NO: 3 are substituted with amino acid residues other than a lysine residue. The amino acid residue other than a lysine residue is preferably an amino acid residue other than a cysteine residue, and specific examples include an arginine residue, a seine residue, a threonine residue, and a glutamic acid residue.

The amino acid sequence represented by SEQ ID NO: 1 may be an amino acid sequence substantially equivalent to the amino acid sequence represented by SEQ ID NO: 1 as long as the effects of the present disclosure can be achieved.

The amino acid sequence substantially equivalent to the amino acid sequence represented by SEQ ID NO: 1 is an amino acid sequence that is not the amino acid sequence represented by SEQ ID NO: 1 but is an amino acid sequence that can achieve the effects of the present disclosure, where the amino acid sequence has a homology of 70% or higher, 75% or higher, 80% or higher, 85% or higher, 90% or higher, or 95% or higher in increasing preference order in comparison of the amino acid sequences excluding the CDR regions of the $V_H$ domain.

Examples of such an amino acid sequence include SEQ ID NO: 18 (homology: 79.3%), SEQ ID NO: 19 (homology: 79.3%), SEQ ID NO: 20 (homology: 88.6%), SEQ ID NO: 21 (homology: 86.2%), SEQ ID NO: 22 (homology: 81.6%), SEQ ID NO: 23 (homology: 81.8%), SEQ ID NO: 24 (homology: 80.5%), and SEQ ID NO: 25 (homology: 81.6%). In addition, amino acid sequences having a homology with each of these amino acid sequences of preferably 85% or higher, more preferably 90% or higher, and even more preferably 95% or higher are also included in the amino acid sequence substantially equivalent to the amino acid sequence represented by SEQ ID NO: 1.

Furthermore, the amino acid sequence represented by SEQ ID NO: 3 may be an amino acid sequence substantially equivalent to the amino acid sequence represented by SEQ ID NO: 3 as long as the effects of the present disclosure can be achieved.

The amino acid sequence substantially equivalent to the amino acid sequence represented by SEQ ID NO: 3 is an amino acid sequence that is not the amino acid sequence represented by SEQ ID NO: 3 but is an amino acid sequence that can achieve the effects of the present disclosure, where the amino acid sequence has a homology of 70% or higher, 75% or higher, 80% or higher, 85% or higher, 90% or higher, or 95% or higher in increasing preference order in comparison of the amino acid sequences excluding the CDR regions of the $V_L$ domain.

Examples of such an amino acid sequence include SEQ ID NO: 26 (homology: 78.0%), SEQ ID NO: 27 (homology: 89.0%), SEQ ID NO: 28 (homology: 86.4%), SEQ ID NO: 29 (homology: 81.3%), SEQ ID NO: 30 (homology: 87.9%), SEQ ID NO: 31 (homology: 85.7%), SEQ ID NO: 32 (homology: 82.4%), and SEQ ID NO: 33 (homology: 92.3%). In addition, amino acid sequences having a homology with each of these amino acid sequences of preferably 85% or higher, more preferably 90% or higher, and even more preferably 95% or higher are also included in the amino acid sequence substantially equivalent to the amino acid sequence represented by SEQ ID NO: 3.

Furthermore, the amino acid sequence substantially equivalent to the amino acid sequence represented by SEQ ID NO: 1 and the amino acid sequence substantially equivalent to the amino acid sequence represented by SEQ ID NO: 3 may be amino acid sequences with a homology score value by BLOSUM 62 of NCBI of 500 or higher, 550 or higher, 600 or higher, 650 or higher, or 700 or higher in increasing preference order, as calculated for the entire amino acid sequence excluding amino acid sequences of the CDR regions of the $V_H$ domain and amino acid sequences of the CDR regions of the $V_L$ domain, assuming that the amino acid sequence represented by SEQ ID NO: 1 and the amino acid sequence represented by SEQ ID NO: 3 are linked. In addition, the amino acid sequence substantially equivalent to the amino acid sequence represented by SEQ ID NO: 1 and the amino acid sequence substantially equivalent to the amino acid sequence represented by SEQ ID NO: 3 may be amino acid sequences with a homology of 70% or higher, 75% or higher, 80% or higher, 85% or higher, 90% or higher, or 95% or higher in increasing preference order, as calculated for the entire amino acid sequence formed by linking, excluding amino acid sequences of the CDR regions of the $V_H$ domain and amino acid sequences of the CDR regions of the $V_L$ domain.

Such amino acid sequences are, for example,

SEQ ID NO: 18 as an amino acid sequence substantially equivalent to the amino acid sequence represented by SEQ ID NO: 1 and SEQ ID NO: 26 as an amino acid sequence substantially equivalent to the amino acid sequence represented by SEQ ID NO: 3 (homology score value: 718 and identity: 78.70%), SEQ ID NO: 19 as an amino acid sequence substantially equivalent to the amino acid sequence represented by SEQ ID NO: 1 and SEQ ID NO: 27 as an amino acid sequence substantially equivalent to the amino acid sequence represented by SEQ ID NO: 3 (homology score value: 762 and identity: 84.30%), SEQ ID NO: 20 as an amino acid sequence substantially equivalent to the amino acid sequence represented by SEQ ID NO: 1 and SEQ ID NO: 28 as an amino acid sequence substantially equivalent to the amino acid sequence represented by SEQ ID NO: 3 (homology score value: 807 and identity: 87.50%), SEQ ID NO: 21 as an amino acid sequence substantially equivalent to the amino acid sequence represented by SEQ ID NO: 1 and SEQ ID NO: 29 as an amino acid sequence substantially equivalent to the amino acid sequence represented by SEQ ID NO: 3 (homology score value: 737 and identity: 80.90%), SEQ ID NO: 22 as an amino acid sequence substantially equivalent to the amino acid sequence represented by SEQ ID NO: 1 and SEQ ID NO: 30 as an amino acid sequence substantially equivalent to the amino acid sequence represented by SEQ ID NO: 3 (homology score value: 763 and identity: 84.80%), SEQ ID NO: 23 as an amino acid sequence substantially equivalent to the amino acid sequence represented by SEQ ID NO: 1 and SEQ ID NO: 31 as an amino acid sequence substantially equivalent to the amino acid sequence represented by SEQ ID NO: 3 (homology score value: 766 and identity: 83.80%), SEQ ID NO: 24 as an amino acid sequence substantially equivalent to the amino acid sequence represented by SEQ ID NO: 1 and SEQ ID NO: 32 as an amino acid sequence substantially equivalent to the amino acid sequence represented by SEQ ID NO: 3 (homology score value: 740 and identity: 81.50%), and SEQ ID NO: 25 as an amino acid sequence substantially equivalent to the amino acid sequence represented by SEQ ID NO: 1 and SEQ ID NO: 33 as an amino acid sequence substantially equivalent to the amino acid sequence represented by SEQ ID NO: 3 (homology score value: 744 and identity: 87.10%).

In addition, each of amino acid sequences having a homology with each of these amino acid sequences of preferably 85% or higher, more preferably 90% or higher, and even more preferably 95% or higher is also included in the amino acid sequence substantially equivalent to the amino acid sequence represented by SEQ ID NO: 1 and the amino acid sequence substantially equivalent to the amino acid sequence represented by SEQ ID NO: 3.

The amino acid sequence represented by SEQ ID NO: 2 may be an amino acid sequence substantially equivalent to the amino acid sequence represented by SEQ ID NO: 2 as long as the effects of the present disclosure can be achieved.

The amino acid sequence substantially equivalent to the amino acid sequence represented by SEQ ID NO: 2 is an amino acid sequence that is not the amino acid sequence represented by SEQ ID NO: 2 but is an amino acid sequence that can achieve the effects of the present disclosure, where the amino acid sequence has a homology of preferably 85% or higher, more preferably 90% or higher, and even more preferably 95% or higher with the amino represented by SEQ ID NO: 2.

The same applies to the amino acid sequence represented by SEQ ID NO: 17 and the amino acid sequence containing three or more lysine residues.

The amino acid sequence represented by SEQ ID NO: 1 and the amino acid sequences substantially identical to the amino acid sequence represented by SEQ ID NO: 1 are shown in FIG. 2-1-1 and FIG. 2-1-2, and the amino acid sequence represented by SEQ ID NO: 3 and the amino acid sequences substantially identical to the amino acid sequence represented by SEQ ID NO: 3 are shown in FIG. 2-2-1 and FIG. 2-2-2. The clone number in each figure is the clone number of each single-chain antibody described in Patent Documents 2 and 3, and each sequence is the sequence of the $V_H$ domain and the $V_L$ domain in each single-chain antibody. CDR regions and FR regions in each domain are also described for understanding.

In addition, the amino acid sequence represented by SEQ ID NO: 1 may be an amino acid sequence in which one or more amino acids of the amino acid sequence represented by SEQ ID NO: 1 is substituted, deleted, inserted, and/or added as long as the effect of the present disclosure can be achieved. "One or more" is from 1 to 12, from 1 to 10, from 1 to 5, or from 1 to 3 in increasing preference order.

In addition, the amino acid sequence represented by SEQ ID NO: 3 may be an amino acid sequence in which one or more amino acids of the amino acid sequence represented by SEQ ID NO: 3 is substituted, deleted, inserted, and/or added as long as the effects of the present disclosure can be achieved. "One or more" is from 1 to 12, from 1 to 10, from 1 to 5, or from 1 to 3 in increasing preference order.

In addition, the amino acid sequence represented by SEQ ID NO: 2 may be an amino acid sequence in which one or more amino acids of the amino acid sequence represented by SEQ ID NO: 2 is substituted, deleted, inserted, and/or added as long as the effects of the present disclosure can be achieved. "One or more" is from 1 to 3, from 1 to 2, or one in increasing preference order.

In addition, the amino acid sequence represented by SEQ ID NO: 17 may be an amino acid sequence in which one or more amino acids of the amino acid sequence represented by SEQ ID NO: 17 is substituted, deleted, inserted, and/or added as long as the effects of the present disclosure can be achieved. "One or more" is from 1 to 3, from 1 to 2, or one in increasing preference order.

In addition, the amino acid sequence containing three or more lysine residues may be an amino acid sequence in which one or more amino acids of the amino acid sequence containing three or more lysine residues is substituted, deleted, inserted, and/or added as long as the effects of the present disclosure can be achieved. "One or more" is from one to [10% of the number of amino acid residues in the amino acid sequence containing three or more lysine residues], from one to [5% of the number of amino acid residues in the amino acid sequence containing three or more lysine residues], from one to [2.5% of the number of the amino acid residues in the amino acid sequence containing three or more lysine residues], from one to [1% of the number of amino acid residues in the amino acid sequence containing three or more lysine residues], or one. A fraction is rounded up.

The substitution, deletion, insertion, and/or addition of one or more amino acids in the amino acid sequence represented by SEQ ID NO: 1 are conservative mutations that maintain the normal function of the protein containing the amino acid sequence represented by SEQ ID NO: 1.

A representative conservative mutation is a conservative substitution. The conservative substitutions are mutual substitutions between Phe, Trp, and Tyr when the substitution site is an aromatic amino acid, between Leu, Ile, and Val when the substitution site is a hydrophobic amino acid, between Gln and Asn when the substitution site is a polar amino acid, between Lys, Arg, and His when the substitution site is a basic amino acid, between Asp and Glu when the substitution site is an acidic amino acid, or between Ser and Thr when the substitution site is an amino acid having a hydroxyl group.

Examples of the conservative substitution specifically include a substitution of Ala with Ser or Thr, a substitution of Arg with Gln, His, or Lys, a substitution of Asn with Glu, Gln, Lys, His, or Asp, a substitution of Asp with Asn, Glu, or Gln, a substitution of Cys with Ser or Ala, a substitution of Gln with Asn, Glu, Lys, His, Asp, or Arg, a substitution of Glu with Gly, Asn, Gln, Lys, or Asp, a substitution of Gly with Pro, a substitution of His with Asn, Lys, Gln, Arg, or Tyr, a substitution of Ile with Leu, Met, Val, or Phe, a substitution of Leu with Ile, Met, Val, or Phe, a substitution of Lys with Asn, Glu, Gln, His, or Arg, a substitution of Met with Ile, Leu, Val, or Phe, a substitution of Phe with Trp, Tyr, Met, Ile, or Leu, a substitution of Ser with Thr or Ala, a substitution of Thr with Ser or Ala, a substitution of Trp with Phe or Tyr, a substitution of Tyr with His, Phe, or Trp, and a substitution of Val with Met, Ile, or Leu.

The same applies to the amino acid sequence represented by SEQ ID NO: 2, the amino acid sequence represented by SEQ ID NO: 17, the amino acid sequence represented by SEQ ID NO: 3, and the amino acid sequence containing three or more lysine residues.

In addition, a tag, such as a His tag, a GST tag, or a FLAG tag, may be attached to the C-terminus of the amino acid sequence containing three or more lysine residues as long as the effects of the present disclosure are achieved. These tags may contain a lysine residue.

The single-chain antibody R3-26 can be obtained by the method described in Patent Documents 2 and 3 or can be also obtained by a known genetic engineering technique, protein engineering technique, or the like.

In addition, a protein containing an amino acid sequence substantially equivalent to the amino acid sequence of the single-chain antibody R3-26 can also be obtained by the method described in Patent Documents 2 and 3 or can be also obtained by modifying the amino acid sequence of the single-chain antibody R3-26 by a known genetic engineering technique, protein engineering technique, or the like.

Whichever the case, any technique can be used without limitation as long as a protein containing the single-chain antibody R3-26 or an amino acid sequence substantially equivalent to the amino acid sequence of the single-chain antibody R3-26 can be consequently obtained.

Furthermore, the protein used in the first aspect of the present disclosure can be obtained by modifying the amino acid sequence of the single-chain antibody R3-26 or an amino acid sequence substantially equivalent to the amino acid sequence of the single-chain antibody R3-26 by a known genetic engineering technique, protein engineering technique, or the like, but any technique can be used without limitation as long as a protein containing the target amino acid sequence can be consequently obtained.

11

[Dynamic Binding Capacity (DBC)]

When the conditions, such as the amount of the protein immobilized on the carrier and the flow rate, are the same, a dynamic binding capacity (DBC) of the separating agent according to the first aspect of the present disclosure is not less than, that is, greater than or equal to a dynamic binding capacity (DBC) of a separating agent in which the single-chain antibody R3-26 is bound to the surface of the carrier via an original lysine residue in the amino acid sequence of the single-chain antibody R3-26.

The dynamic binding capacity (DBC) of the separating agent according to the first aspect of the present disclosure expressed, for example, as a value of [10% DBC (mg/mL) at a flow rate of 1.0 mL/min]/[an amount of the protein immobilized on a column (mg)] is preferably 1.00-fold or greater, more preferably 1.20-fold or greater, even more preferably 1.40-fold or greater, and still more preferably 1.60-fold or greater than that of a separating agent in which the single-chain antibody R3-26 is bound to the surface of the carrier via an original lysine residue in the amino acid sequence of the single-chain antibody R3-26.

The dynamic binding capacity (DBC) of the separating agent according to the first aspect of the present disclosure can be measured by a known method, for example, a method described in Examples.

2. Second Aspect of Disclosure

A second aspect of the present disclosure is a method for separating a water-soluble substance with the protein bound from a mixed liquid of two or more water-soluble substances using the separating agent according to the first aspect of the present disclosure.

One of the two or more water-soluble substances is preferably a human serum-derived IgG polyclonal antibody and more preferably one or more antibodies selected from the group consisting of a human serum-derived IgG1 polyclonal antibody, a human serum-derived IgG2 polyclonal antibody, a human serum-derived IgG3 polyclonal antibody, and a human serum-derived IgG4 polyclonal antibody, which are subtypes of a human serum-derived IgG polyclonal antibody.

The method according to the second aspect of the present disclosure can analyze a sample and separate a water-soluble substance with the protein bound from a sample by an operation similar to a typical affinity chromatography in which an antibody is immobilized on a carrier, in addition to the operation under conditions suitable for separating a water-soluble substance.

3. Third Aspect of Disclosure

Another aspect of the present disclosure is
a protein containing:
an amino acid sequence represented by SEQ ID NO: 1, an amino acid sequence represented by SEQ ID NO: 2, and an amino acid sequence represented by SEQ ID NO: 3 arranged sequentially from the N-terminus; or
an amino acid sequence represented by SEQ ID NO: 3, an amino acid sequence represented by SEQ ID NO: 17, and an amino acid sequence represented by SEQ ID NO: 1 arranged sequentially from the N-terminus; and
an amino acid sequence containing three or more lysine residues at the C-terminus;
wherein all lysine residues contained in the amino acid sequence represented by SEQ ID NO: 1, the amino acid sequence represented by SEQ ID NO: 2, the amino acid sequence represented by SEQ ID NO: 17, and the amino acid sequence represented by SEQ ID NO: 3 are substituted with amino acid residues other than a lysine residue.

For details of the protein according to the present aspect, the description in the section "Protein" in the description of the first aspect of the present disclosure is cited.

Thus, the protein according to the present aspect has an activity of binding to a human serum-derived IgG polyclonal antibody. Furthermore, the protein has an activity of binding to one or more antibodies selected from the group consisting of a human serum-derived IgG1 polyclonal antibody, a human serum-derived IgG2 polyclonal antibody, a human serum-derived IgG3 polyclonal antibody, and a human serum-derived IgG4 polyclonal antibody, which are subtypes of a human serum-derived IgG polyclonal antibody.

EXAMPLES

Hereinafter, the present disclosure will be described more specifically with reference to examples, but the present disclosure is not limited to the following examples as long as the gist of the present disclosure is not deviated.

Production Example 1

A vector for expressing a protein was constructed from DNA (SEQ ID NO: 9) encoding a protein containing the protein (the single-chain antibody R3-26 described in Patent Documents 2 and 3) containing the amino acid sequence represented by SEQ ID NO: 1, the amino acid sequence represented by SEQ ID NO: 2, and the amino acid sequence represented by SEQ ID NO: 3 arranged sequentially from the N-terminus, and a linker amino acid sequence represented by SEQ ID NO: 4 at the C-terminus with reference to Patent Documents 2 and 3.

The amino acid sequence containing the protein containing the amino acid sequence represented by SEQ ID NO: 1, the amino acid sequence represented by SEQ ID NO: 2, and the amino acid sequence represented by SEQ ID NO: 3 arranged sequentially from the N-terminus, and the linker amino acid sequence represented by SEQ ID NO: 4 at the C-terminus is shown as SEQ ID NO: 5.

The constructed expression vector is expressed in a form in which a periplasm migration signal (pelB leader signal) sequence is fused to the N-terminus, and a histidine tag (6×His-tag) is fused to the C-terminus side of the linker amino acid sequence represented by SEQ ID NO: 4. After the expression, the protein migrates to the periplasm, and the pelB leader signal sequence is cleaved by a signal peptidase.

The constructed expression vector was used to transform *Escherichia coli* Rosetta (DE3), and the transformed *Escherichia coli* was cultured on an LB agar plate (50 mg/L ampicillin). The resulting single colony was cultured overnight in 10 mL of an LB medium (50 mg/L ampicillin). The resulting culture liquid was inoculated in 50 mL of Overnight Express TB medium (Merck KGaA) and incubated at 37° C. and 200 rpm for 24 hours.

The resulting culture liquid was centrifuged (10000 rpm, 4° C., 15 minutes), and a culture supernatant was obtained. The culture supernatant was filtered through a 0.45 μm pore size hydrophilic Durapore membrane (Merck KGaA), the filtrate was applied to a HisTrap FF crude column (GE Healthcare), and the protein was captured on the column. The captured protein was eluted using 0.4 M imidazole. In addition, the protein concentration after elution was quantified by DC Protein assay (Biorad). Furthermore, the purity of the protein in the eluant was determined by SDS-PAGE. The solvent of the collected protein solution was replaced with PBST, and the dissociation constant $K_D$ was measured with Biacore X-100 as described later.

Production Example 2

The protein containing the amino acid sequence represented by SEQ ID NO: 5 used in Production Example 1 was modified as follows. The modified protein is referred to as "R3-26 repCK+K" and its amino acid sequence is shown as SEQ ID NO: 6.
- In the amino acid sequence represented by SEQ ID NO: 1, the lysine residue at position 14 designated by the IMGT numbering was substituted with a threonine residue, the lysine residue at position 48 designated by the IMGT numbering was substituted with a glutamic acid residue, and the lysine residues at positions 72, 80, and 90 designated by the IMGT numbering were substituted with arginine residues.
- In the amino acid sequence represented by SEQ ID NO: 2, amino acid residues were not substituted.
- In the amino acid sequence represented by SEQ ID NO: 3, the lysine residue at position 22 designated by the IMGT numbering was substituted with an asparagine residue, the lysine residue at position 51 designated by the IMGT numbering was substituted with an arginine residue, the lysine residue at position 77 designated by the IMGT numbering was substituted with a serine residue, and the cysteine residue at position 96 designated by the IMGT numbering was substituted with a serine residue.
- The amino acid sequence represented by SEQ ID NO: 4 was changed to AAAGGGGSKIE (SEQ ID NO: 14) sequentially from the N-terminus side to the C-terminus side.

In addition, the base sequence of the DNA encoding the amino acid sequence of R3-26 repCK+K is shown as SEQ ID NO: 10.

Production Example 3

The protein containing the amino acid sequence represented by SEQ ID NO: 5 used in Production Example 1 was modified as follows. The modified protein is referred to as "R3-26 repCK+K3" and its amino acid sequence is shown as SEQ ID NO: 7.

The procedure was performed in the same manner as in Production Example 2 except for changing the amino acid sequence represented by SEQ ID NO: 4 in Production Example 2 to AAAGGGGSKKKIE (SEQ ID NO: 15).

In addition, the base sequence of the DNA encoding the amino acid sequence of R3-26 repCK+K3 is shown as SEQ ID NO: 11.

Production Example 4

The protein containing the amino acid sequence represented by SEQ ID NO: 5 used in Production Example 1 was modified as follows. The modified protein is referred to as "R3-26 repCK+K5" and its amino acid sequence is shown as SEQ ID NO: 8.

The procedure was performed in the same manner as in Production Example 2 except for changing the amino acid sequence represented by SEQ ID NO: 4 in Production Example 2 to AAAGGGGSKKKKKIE (SEQ ID NO: 16).

In addition, the base sequence of the DNA encoding the amino acid sequence of R3-26 repCK+K5 is shown as SEQ ID NO: 12.

The measurement of the dissociation constant $K_D$ using the proteins obtained in Production Examples 1 to 4 was performed under the following measurement conditions.
Sensor chip: human IgG1-coupled CM5
Running buffer: PBST
Binding time: 180 sec
Dissociation time: 600 to 800 sec
Elution: 10 mM Glycine, pH 1.5
Mode: Single cycle kinetics mode The measurement results of yield at preparation and the dissociation constant $K_D$ of the proteins obtained in Production Examples 1 to 4 are summarized in Table 1. In comparison with the protein obtained in Production Example 1, no decrease in production quantity was observed for any of the proteins obtained in Production Examples 2 to 4, and the dissociation constant $K_D$ was in the same order.

The above results showed that the modification of the amino acid sequence does not cause a significant decrease in the productivity and the binding capacity indicated by the dissociation constant $K_D$.

[Table 1]

TABLE 1

|  | Production quantity per 1 L of medium (g/L) | Human IgG immobilized amount (RU) | $K_{on}$ ($M^{-1}s^{-1}$) | $K_{off}$ ($s^{-1}$) | $K_D$ (M) | $R_{max}$ (RU) |
|---|---|---|---|---|---|---|
| Production Example 1 | 0.10 | 5000 | $2.1 \times 10^4$ | $4.3 \times 10^{-5}$ | $2.1 \times 10^{-9}$ | 329.4 |
| Production Example 2 | 0.23 | 2050 | $5.6 \times 10^4$ | $9.1 \times 10^{-5}$ | $1.6 \times 10^{-9}$ | 128.2 |
| Production Example 3 | 0.19 | 2050 | $6.1 \times 10^4$ | $1.0 \times 10^{-4}$ | $1.7 \times 10^{-9}$ | 121.7 |
| Production Example 4 | 0.26 | 2050 | $7.0 \times 10^4$ | $1.7 \times 10^{-4}$ | $2.4 \times 10^{-9}$ | 144.5 |

Reference Example 1-1

The procedure was performed in the same manner as in Production Example 1, and the solvent of the protein solution collected by ultrafiltration was replaced with 0.2 M sodium hydrogen carbonate buffer (pH 8.3) containing 0.5 M NaCl.

(Immobilization of Protein on Carrier)

The purified protein was supplied to a HiTrap NHS-activated HP Column 1 mL (GE Healthcare) and immobilized via an amino group of lysine residues contained in the protein. An unreacted NHS ester was blocked by adding tris-hydroxymethylaminomethane. The amount of the protein immobilized on the column was 4.0 mg.

(Measurement of Dynamic Binding Capacity)

The column with the protein immobilized thereon was set in a chromatography system AKTA Purifier UPC 10 (GH Healthcare) and equilibrated with PBS. A human serum-derived IgG polyclonal antibody (WAKO) prepared at 1 mg/mL was continuously supplied at a flow rate of 1 mL/min, and a breakthrough curve was obtained. From the elution capacity at 10% breakthrough point of the resulting breakthrough curve, a 10% dynamic binding capacity (DBC) was calculated.

Reference Example 1-2

The procedure was performed in the same manner as in Reference Example 1-1 except for changing the amount of the protein immobilized on the column to 5.0 mg.

Comparative Example 1

The procedure was performed in the same manner as in Reference Example 1-1 except for using the protein "R3-26 repCK+K" produced in Production Example 2 as the protein.

Example 1-1

The procedure was performed in the same manner as in Reference Example 1-1 except for using the protein "R3-26 repCK+K3" produced in Production Example 3 as the protein and changing the immobilized amount to 5.0 mg.

Example 1-2

The procedure was performed in the same manner as in Reference Example 1-1 except for using the protein "R3-26 repCK+K5" produced in Production Example 4 as the protein and changing the immobilized amount to 5.0 mg.

Results

The results are summarized in Table 2. The result of Reference Example in the table is the average value of the results of Reference Example 1-1 and Reference Example 1-2.

The DBC value per amount of the immobilized protein was greater in Example 1-1 and Example 1-2 than in Reference Example. On the other hand, the DBC value per amount of the immobilized protein was smaller in Comparative Example 1 than in Reference Example.

The above results demonstrate that binding only one lysine residue to the surface of the carrier by a chemical bond does not improve the capture efficiency for the target substance on the carrier, but binding three or more lysine residues to the surface of the carrier by chemical bonds improves the capture efficiency for the target substance on the carrier.

[Table 2]

TABLE 2

| | [10% DBC (mg/mL) at flow rate of 1.0 mL/min]/ [amount of protein immobilized on column (mg)] |
|---|---|
| Reference Example | 0.86 |
| Comparative Example 1 | 0.63 |
| Example 1-1 | 1.26 |
| Example 1-2 | 1.40 |

Reference Example 2

The procedure was performed in the same manner as in Reference Example 1-1 except for changing the amount of the protein immobilized on the column to a wide range of amounts.

Example 2

The procedure was performed in the same manner as in Reference Example 1-1 except for changing the amount of the protein "R3-26 repCK+K5" produced in Production Example 4 immobilized on the column to a wide range of amounts.

Results

The results are shown in FIG. 1. The dashed line in the figure is the approximate straight line of the resulting plot.

The results showed that the capture efficiency of the target substance was higher in Example 2 than in Reference Example 2 over a wide range of the immobilized amount.

---

The invention claimed is:

1. A separating agent comprising a carrier and a protein, wherein the protein comprised in the separating agent is a single chain antibody (scFv) comprising:
(a) a first amino acid sequence of SEQ ID NO: 1 or an amino acid sequence that has a homology of 70% or higher thereof, a second amino acid sequence of SEQ ID NO: 2 or an amino acid sequence that has a homology of 85% or higher thereof, and a third amino acid sequence of SEQ ID NO: 3 or an amino acid sequence that has a homology of 70% or higher thereof arranged sequentially from the N-terminus; or a first amino acid sequence of SEQ ID NO: 3 or an amino acid sequence that has a homology of 70% or higher thereof, a second amino acid sequence of SEQ ID NO: 17 or an amino acid sequence that has a homology of 85% or higher thereof, and a third amino acid sequence of SEQ ID NO: 1 or an amino acid sequence that has a homology of 70% or higher thereof arranged sequentially from the N-terminus; and
(b) a fourth amino acid sequence comprising three or more lysine residues, wherein the fourth amino acid sequence is linked to the C-terminus of the amino acid sequence of (a), wherein said fourth amino acid sequence is 15 or fewer amino acid residues in length and comprises the amino acid sequence according to SEQ ID NO: 13 present on the N-terminus side of consecutive three or more lysine residues and the amino acid residues IE are present on the C-terminus side of said three or more lysine residues; wherein all lysine residues contained in the amino acid sequence of SEQ ID NO: 1 or an amino acid sequence that has a homology of 70% or higher thereof, the amino acid sequence of SEQ ID NO: 2 or an amino acid sequence that has a homology of 85% or higher thereof, the amino acid sequence of SEQ ID NO: 17 or an amino acid sequence that has a homology of 85% or higher thereof, and the amino acid sequence of SEQ ID NO: 3 or an amino acid sequence that has a homology of 70% or higher thereof are substituted with amino acid residues other than a lysine residue; and a surface of the carrier and lysine residues in said fourth amino acid sequence are bound by chemical bonds.

2. A method for separating a water-soluble target substance from a liquid comprising two or more water-soluble substances, the method comprising contacting a liquid comprising two or more water-soluble substances with the separating agent according to claim 1.

3. A single chain antibody (scFv) comprising:
(a) a first amino acid sequence of SEQ ID NO: 1 or an amino acid sequence that has a homology of 70% or higher thereof, a second amino acid sequence of SEQ ID NO: 2 or an amino acid sequence that has a homology of 85% or higher thereof, and a third amino acid sequence of SEQ ID NO: 3 or an amino acid sequence that has a homology of 70% or higher thereof arranged sequentially from the N-terminus; or a first amino acid sequence of SEQ ID NO: 3 or an amino acid sequence that has a homology of 70% or higher thereof, a second amino acid sequence of SEQ ID NO: 17 or an amino acid sequence that has a homology of 85% or higher thereof, and a third amino acid sequence of SEQ ID NO: 1 or an amino acid sequence that has a homology of 70% or higher thereof arranged sequentially from the N-terminus; and
(b) a fourth amino acid sequence comprising three or more lysine residues, wherein the fourth amino acid sequence is linked to the C-terminus of the amino acid sequence of (a), wherein said fourth amino acid sequence is 15 or fewer amino acid residues in length and comprises the amino acid sequence according to SEQ ID NO: 13 present on the N-terminus side of consecutive three or more lysine residues and the amino acid residues IE are present on the C-terminus side of said three or more lysine residues;

wherein all lysine residues contained in the amino acid sequence of SEQ ID NO: 1 or an amino acid sequence that has a homology of 70% or higher thereof, the amino acid sequence of SEQ ID NO: 2 or an amino acid sequence that has a homology of 85% or higher thereof, the amino acid sequence of SEQ ID NO: 17 or an amino acid sequence that has a homology of 85% or higher thereof, and the amino acid sequence of SEQ ID NO: 3 or an amino acid sequence that has a homology of 70% or higher thereof are substituted with amino acid residues other than a lysine residue.

4. The separating agent according to claim 1, wherein said fourth amino acid sequence is the sequence of SEQ ID NO: 15 or SEQ ID NO: 16.

5. The single chain antibody (scFv) according to claim 3, wherein said fourth amino acid sequence is the sequence of SEQ ID NO: 15 or SEQ ID NO: 16.

\* \* \* \* \*